United States Patent [19]

Tong et al.

[11] Patent Number: 5,637,735

[45] Date of Patent: Jun. 10, 1997

[54] PROCESS FOR THE PREPARATION OF GAMMA-BUTYROLACTONE

[75] Inventors: Lishan Tong; Haijing Wang; Weisun Feng; Guoqiang Gao; Xiangwei Li; Jinghui Deng; Xinjie Zhang, all of Beijing, China

[73] Assignees: China Petrochemical Corporation; Research Institute of Petroleum Processing SINOPEC, both of China, China

[21] Appl. No.: 512,899

[22] Filed: Aug. 9, 1995

[30] Foreign Application Priority Data

Aug. 10, 1994 [CN] China ............... CN94108093.5

[51] Int. Cl.$^6$ ............................................. C07D 307/33
[52] U.S. Cl. ................................ 549/325; 502/307
[58] Field of Search ............................................. 549/325

[56] References Cited

U.S. PATENT DOCUMENTS

| | | | |
|---|---|---|---|
| 2,772,291 | 11/1956 | McShane, Jr. et al. | 549/325 |
| 2,772,293 | 11/1956 | Gilbert et al. | 549/325 |
| 3,065,243 | 11/1962 | Dunlop et al. | 549/325 |
| 3,580,930 | 5/1971 | Miya et al. | 549/325 |
| 3,829,448 | 8/1974 | Kanetaka et al. | 549/325 |
| 3,853,922 | 12/1974 | Yamaguchi et al. | 549/325 |
| 4,001,282 | 1/1977 | Miller | 549/325 |
| 4,668,654 | 5/1987 | Drake et al. | 549/325 |

FOREIGN PATENT DOCUMENTS

| | | |
|---|---|---|
| 1034541A | 8/1990 | China . |
| 1058400A | 2/1992 | China . |
| 0332140A2 | 9/1989 | European Pat. Off. . |
| 0404408A1 | 12/1990 | European Pat. Off. . |
| 1168220 | 10/1969 | United Kingdom . |
| WO91/16132 | 10/1991 | WIPO . |
| 95/22539 | 8/1995 | WIPO . |

OTHER PUBLICATIONS

Article entitled, "Vapour Phase Hydrogenation of Maleic Anhydride to γ-Butyrolactone" by G.L. Castiglioni et al., Wissenschaft & Technik, 1994, pp. 146–149.

*Primary Examiner*—Bernard Dentz
*Attorney, Agent, or Firm*—Steven P. Shurtz; Brinks Hofer Gilson & Lione

[57] ABSTRACT

A process for vapor phase hydrogenation of maleic anhydride and/or succinic anhydride to γ-butyrolactone, comprising contacting an alcoholic solution of a feedstock anhydride with reduced Cu-Zn-Cr-Zr catalyst under the conditions of hydrogenation.

14 Claims, No Drawings

PROCESS FOR THE PREPARATION OF GAMMA-BUTYROLACTONE

This invention relates to a process for the preparation of γ-butyrolactone and to the catalyst used in the process, more particularly, to a process of vapor phase catalytic hydrogenation of maleic anhydride and/or succinic anhydride to γ-butyrolactone, and to a catalyst comprising Cu, Zn and Cr which is used in the process.

γ-butyrolactone is an excellent high boiling solvent and an important feedstock in fine chemical and organic chemical industries, and it is widely used in the fields of fiber, resin, petroleum, cosmetics, perfumery, pharmaceuticals, pesticide, photography, dyestuff, pigments and the like, and it is mainly used in the production of pyrrolidone, N-methyl-α-pyrrolidone, N-vinyl-α-pyrrolidone, polyvinylpyrrolidone, α-acetyl-γ butyrolactone, chlorophenoxy-butanoic acid type herbicides or the like.

Prior art teaches that, γ-butyrolactone can be produced by catalytic dehydrogenation of 1,4-butanediol. But the starting 1,4-butanediol is produced by first reacting ethyne and formaldehyde in the presence of cuprous acetylide complex to yield butynediol, and then by reducting thereof. Obviously, such a process for preparing γ-butyrolactone is not economical. Thus, a process for preparing γ-butyrolactone by liquid phase catalytic hydrogenation of the anhydride or ester derivatives of maleic acid or fumaric acid or succinic acid is developed (U.S. Pat. No. 2,772,291; U.S. Pat. No. 2,772,293; U.S. Pat. No. 3,829,448; U.S. Pat. No. 3,853,922). Nevertheless, this liquid phase hydrogenation process needs to be carried out at high temperature and high pressure, and the thus-obtained yield is generally not satisfactory. Thus, a vapor phase catalytic hydrogenation process with the same anhydride or ester derivatives as the starting materials was developed.

U.S. Pat. No. 3,065,243 discloses a process of vapor phase hydrogenation of maleic anhydride, succinic anhydride, or an acid or ester thereof in the presence of Cu-Cr catalyst, however, the conversion and the selectivity to γ-butyrolactone are relatively low.

GB 1,168,220 discloses a process for the preparation of γ-butyrolactone, wherein maleic anhydride or an ester of maleic acid, succinic anhydride or an ester of succinic acid or an ester of fumaric acid is hydrogenated in the vapor phase in the presence of a copper-zinc catalyst to obtain γ-butyrolactone. In this patent, it is suggested that, because maleic anhydride or succinic anhydride is solid at room temperature, it is advantageous to dissolve them in a suitable organic solvent, preferably in γ-butyrolactone when they are used as starting materials. Under the conditions of a weight ratio of solvent γ-butyrolactone to anhydride of 1:1, a reaction temperature of 240°~250° C., a molar ratio of hydogen to anhydride of 60–70 and a feed weight hourly space velocity of 0.003–0.004 hour$^{-1}$, the yield of γ-butyrolactone can be 94~95 mol %; In the case where butanol is used as solvent, and under the conditions of a weight ratio of solvent butanol to anhydride of 4:6, a reaction temperature of 255° C., a molar ratio of hydrogen to anhydride of 60, and a feed weight hourly space velocity of 0.014 hour$^{-1}$, the yield of γ-butyrolactone is only 87 mol %. In this patent, it is particularly emphasised that among the Cu-Zn catalysts involved in this patent, if appropriate, a small amount of auxiliary may be added, but Cr can never be added, or else it will lead to the decrease in the product yield and the increase in the desired reaction temperature. To prove this, the following data are provided in this patent: when Cr content in Cu-Zn catalyst was progressively increased from zero to 50% by weight, the yield of γ-butyrolactone decreased gradually from 95 mol % to 38 mol %, and at the same time, the desired reaction temperature increased gradually from 245° C. to 310° C.

U.S. Pat. No. 3,580,930 discloses a process of vapor phase hydrogenation using Cu-Zn-Cr catalyst in an attempt to minimize the production of by-products, but the yield of the obtained γ-butyrolactone is also very low.

U.S. Pat. No. 4,001,282 describes a vapor phase reaction using Cu-Cr, Cu-Zn or Cu-Zn-Cr catalysts in the presence of water, but the existence of water has greatly increased the complexity of the process.

EP 332,140A discloses a process of vapor phase hydrogenation of maleic anhydride to tetrahydrfuran and γ-butyrolactone using Cu-Zn-Cr-Al catalyst, but the selectivity to γ-butyrolactone is only 50% or even less.

CN 1034541A discloses a process for the preparation of tetrahydrofuran and γ-butyrolactone by vapor phase hydrogenation of maleic anhydride and/or succinic anhydride by contacting with Cu-Zn-Al-M catalyst (M is at least one element selected from the group consisting of II A, III A, V A, VIII, Ag, Au, III~VII B, lanthanide, and actinium series). In accordance with this process, an anhydride is at first vaporized in hot, hydrogen containing gas stream, and then contacts with catalyst for less than 1 minute under the conditions of a reaction temperature of 200°~400° C., a hydrogen pressure of 1~100 atmosphere and a molar ratio hydrogen to anhydride of 10~1000:1. By adjusting operation parameters, the ratio of the yield of tetrahydrofuran to that of γ-butyrolactone in the products can be adjusted, the overall yield of the two can be 90 mol % or more. An example shows that when the volume hourly space velocity of anhydride is <0.27 hour$^{-1}$, the highest yield of γ-butyrolactone is 51.3%.

WO 91/16132A discloses a process of vapor phase hydrogenation of maleic acid or anhydride, succinic acid or anhydride, or their mixture by contacting with Cu-Zn-Al catalyst to produce γ-butyrolactone. In accordance with this process, the molten liquid of feed anhydride passes through a spray nozzle to form finely divided droplets, which are first vaporized in hot, recycle hydrogen gas stream with a molar ratio of hydrogen to anhydride of 200~500:1, and then contact with catalyst for less than 10 seconds under the conditions of 50~500 psig, 200°~400° C. and feed liquid hourly space velocity of 0.03~1.0 hour$^{-1}$. The conversion of feedstock is above 95%, and the selectivity to γ-butyrolactone is above 80%. In this patent, it is pointed out that the catalyst used needs to be activated after the first 100 hours of running and activated again after about 500 hours, whereby the duration of such catalyst can be up to 2000 hours or more. The activation of catalyst must be carried out in situ under hydrogen atmosphere at a temperature of 425°~450° C. for 8~12 hours.

CN 1058400A discloses a process of vapor phase hydrogenation of maleic anhydride and/or succinic anhydride at normal pressure by contacting with Cu-Zn-Al-M catalyst (M is at least one element selected from the group consisting of Ni, Ru, Ce and Zr) to produce γ-butyrolactone. In accordance with this process, the feedstock anhydride is fed in vapor phase directly without having to be dissolved in an organic solvent, and contacts with catalyst under the conditions of normal pressure, 200°~350° C. and a molar ratio of hydrogen to anhydride of 5~200:1 for 2~10 seconds. Conversion of the feedstock anhydride is above 99%, for example 99.6%, 99.9%; and selectivity to product γ-butyrolactone is above 80%, such as 82.9%, 85.1%.

Although the above-mentioned prior arts have their individual characteristics, each has its own drawbacks, for example, the feed hourly space velocity is not sufficiently high, the yield of γ-butyrolactone is not sufficiently high, and the duration of catalyst is not desirable even after reactivation.

One of the objects of the present invention is to provide a process for vapor phase catalytic hydrogenation of maleic anhydride and/or succinic anhydride to γ-butyrolactone at a high feed hourly space velocity and with a high selectivity. Another object of this invention is to provide a hydrogenation catalyst with prolonged duration suitable for producing γ-butyrolactone at a high feed hourly space velocity and with a high selectivity, the said catalyst is capable of regeneration without having to be activated frequently. Other objects of this invention can be learned from the content of the specification including examples.

The process provided by this invention is carried out by vaporizing a solution of the feedstock anhydride and a saturated $C_1$~$C_4$ monohydric alcohol at a molar ratio of 1:1~4, then contacting with a pre-reduced Cu-Zn-Cr-Zr catalyst under hydrogen gas atmosphere under the conditions of a molar ratio of hydrogen to anhydride of 50~300, the temperature range between 200° and 300° C., the pressure range between 0.1 and 2.0 MPa and a liquid hourly space velocity of feedstock anhydride of 0.04~0.30 hour$^{-1}$.

The catalyst provided by this invention has the following oxide formula: $Cu_aZnCr_bZr_cO_x$, wherein a, b and c represent the atom number of Cu, Cr and Zr respectively, a=0.1~10, b=c=0.1~5, and x is the number of oxygen atoms necessary to satisfy the valency requirements of the other metal elements.

In accordance with the process provided by this invention, γ-butyrolactone can be produced by vaporizing an alcoholic solution of anhydride selected from feedstock maleic anhydride and/or succinic anhydride and a saturated $C_1$~$C_4$ monohydric alcohol at a molar ratio of 1:1~4, then feeding it continuously with excess hydrogen into a fixed bed reactor packed with a pre-reduced Cu-Zn-Cr-Zr catalyst for reaction, which is carried out under the following conditions: a molar ratio of hydrogen to anhydride of 50~300, the temperature range between 200° and 300° C., the pressure range between 0.1 and 2.0 MPa and a liquid hourly space velocity of feedstock anhydride of 0.04~0.30 hour$^{-1}$. After the completion of the reaction, the effluent is separated by condensation and rectification to obtain the title product γ-butyrolactone and a small amount of by-products, i.e. tetrahydrofuran and 1,4-butanediol, the excess alcohol and hydrogen are recovered for use in circulation.

Vaporization of said alcoholic solution of anhydride can be performed according to any means disclosed in prior art, the most frequently used way is to vaporize an alcoholic solution of anhydride in hot, hydrogen containing gas stream, and then contact the mixture with a catalyst.

Based on the chemical reaction of hydrogenation of anhydride, hydrogenation of one mole of anhydride to γ-butyrolactone requires only 3 moles of hydrogen. But because of the poor heat stability of the feedstock anhydride, the overall process of the vaporization-reaction is carried out preferably under an atmosphere of excess of hydrogen in order that the reaction materials can be vaporized at lower temperature. However, over-excessive hydrogen will not only reduce the contact time of the reactants with the catalyst but also increase the consumption of energy. In the process provided by this invention, the molar ratio of hydrogen to anhydride shall preferably be 50~300. After the reaction, the excess of hydrogen, together with fresh hydrogen, returns to the reactor for use in circulatiion.

To ensure the reaction being carried out in vapor phase, the reaction temperature must be higher than the dew point of the reactants under such reaction conditions. However, since γ-butyrolactone is an intermediate product of hydrogenation of maleic anhydride and/or succinic anhydride and will lead to tetrahydrofuran, 1,4-butanediol and n-butanol while being further hydrogenated and dehydrated, the reaction temperature can not be too high in order to avoid the increase in high hydrogenation products; to the contrary, if the reaction temperature is too low (even if higher than the dew point of the reactants), the conversion will decrease too. The reaction temperature which is most compatible with the catalyst used in the present process is 200°~300° C.

The increase in the reaction pressure in the present reaction system is advantageous to improve the reactivity of the catalyst, but it will also accelerate the reaction equilibrium to move from γ-butyrolactone towards 1,4-butanediol. Generally, the hydrogenation of maleic anhydride and/or succinic anhydride to γ-butyrolactone can be carried out at normal pressure, but in order to facilitate industrial application, especially in consideration of the circulation of hydrogen, the selected pressure in the present process is 0.3~2.0 MPa.

In the present process, a higher feed liquid hourly space velocity of feedstock anhydride of 0.04~0.30 hour$^{-1}$ compatible with the catalyst used is adopted. Although still higher feed hourly space velocity is one of the main objects pursued by industrialization, overhigh feed hourly space velocity will inevitably lead to the decrease in the contact time of the reactants with the catalyst, and will further influence the conversion of the reaction since the reaction is carried out at high molar ratio of hydrogen to anhydride. Therefore, the increase in feed hourly space velocity is subject to high molar ratio of hydrogen to anhydride.

The process provided by the present invention is carried out in a fixed bed reactor, which can be either a single reactor or a reactor group consisting of two cascade reactors. In the case of cascade reactor group, the feed hourly space velocity in the first reactor should be at least twice as much as that in the second reactor.

The catalyst which is compatible with the present process has the following oxide formula: $Cu_aZnCr_bZr_cO_x$, wherein a, b and c represent the atom number of Cu, Cr and Zr respectively, a=0.1~10, b=c=0.1~5, and x is the number of oxygen atoms necessary to satisfy the valency requirements of the other metal elements.

The said catalyst is obtained by using a general co-precipitation technology, that is, particularly, nitrates of Cu, Zn and Zr and chromic anhydride are dissolved in water according to their respective proportions in the composition of the catalyst, and the solution of the said metal salts is co-precipitated with base or aqueous ammonia, then the precipitate is filtered off, washed, dried at a temperature of 100°–120° C., calcinated at a temperature of 350°~500° C., and molded.

The catalyst should be pre-reduced before being used in the catalytic reaction. The reduction is carried out in situ in a reactor under hydrogen or a inert gas diluted hydrogen at a temperature of 150°~300° C. and a pressure of 0.1~2.0 MPa for 5~40 hours.

After continuous operation for several thousand hours, there will be certain decrease in the activity of the catalyst, which, however, will recover to the same level as that of a fresh catalyst only by regeneration with oxygen gas at a temperature of <300° C. and the reduction treatment in situ as mentioned above.

Because of the use of the said catalyst with special composition and the said feed manner of the alcoholic solution, the process provided by the present invention can be performed at a feed hourly space velocity higher than that in prior art and with a conversion of anhydride of nearly 100% and a selectivity to γ-butyrolactone of above 85%. The said catalyst possesses a prolonged service life of up to 1500~2000 hours, and a low regeneration temperature of less than 300° C., moreover, the activity of the catalyst can, after regeneration, recover to the same level as that of a fresh catalyst. All these properties bring about great advantages to industrial production.

The following examples will illustrate the present invention in detail, but they shall not be used to limit the scope of the present invention.

In the examples, the liquid hourly space velocity is defined as the volume of liquid anhydride per hour per unit volume of catalyst used in the reactor at a temperature of 70° C. and at a pressure of 0.1 MPa.

EXAMPLE 1

Preparation of Catalyst 261 g of copper nitrate (product from Beijing Chemical Plant, chemically pure), 298 g of zinc nitrate (product from Beijing Chemical Plant, chemically pure), 116 g of chromic anhydride (product from Beijing Chemical Plant, chemically pure) and 134 g of zirconium nitrate (product from Beijing Chemical Plant, chemically pure) were dissolved in 1000 ml of de-ionized water and stirred into a homogeneous mixture before aqueous ammonia was added. The pH of the mixture was adjusted to 6±1, then precipitate occurred. The precipitate was filtered off, washed, dried at 110°±10° C. for 12 hours, calcinated at 400°±50° C. for 24 hours, and then molded. The product catalyst particles, φ 2.5 mm×2 mm in diameter, have a pressure resistant strength of >100 N/cm (measured according to the method described in "Analysis Method in Petroleum Chemical Industry (RIPP Test Method)", Science Press, 1990, p66) were obtained.

Pre-reduction of Catalyst 62.5 ml of the said catalyst particles prepared above was packed into the latter half portion of a stainless steel tubular reactor having an internal diameter of φ 23 mm and a length of 1000 mm, and the fore half portion of which was filled with a 20 mesh stainless steel screen for use as a feed vaporizer during the reaction. Nitrogen gas was blown into the reaction system to a pressure of 0.8 MPa. Hydrogen diluted with nitrogen was introduced into the reactor at a flow capacity of 2.5 cubic liters/min, with the concentration of hydrogen increasing gradually from 2% to 100% by volume. Meanwhile, the catalyst was pre-reduced by raising the temperature of the reactor from room temperature to 295°±5° C. at an average speed of less than 20° C. per hour, for a total reduction time of 40 hours.

Catalytic Reaction

The reaction of a solution of maleic anhydride and n-butanol (both the anhydride and the alcohol are commercial products with industrial grade) at a molar ratio of anhydride to alcohol of 1:2.5 was carried out at a vaporization temperature of 230° C. under the following conditions: 0.8 MPa, 270°±5° C., the liquid hourly space velocity of the feedstock anhydride of 0.1 hour$^{-1}$, the molar ratio of hydrogen to anhydride of 250:1. The reaction ran continuously for 1055 hours. The reaction product between 1031 and 1041 hours and the reaction product between 1041 and 1055 hours taken from the reactor were analyzed by chromatography, and the results were similar: the conversion of maleic anhydride was 98 mol %; the selectivity to product γ-butyrolactone was 92 mol %; and the selectivities to such by-products as tetrahydrofuran and 1,4-butanediol were 6 mol % and 2 mol % respectively.

EXAMPLE 2

The catalyst was prepared according to the process described in example 1, except that the amounts of the reactants were increased by 212 times, thus, the external dimensions of the catalyst particles were increased to φ 5 mm×3 mm.

A stainless steel fixed bed reactor having a height of 5 m was packed with 1 m$^3$ of the said catalyst, wherein the height of the catalyst bed was 3.6 m. After nitrogen gas was blown into the reaction system, the concentration of hydrogen was raised gradually from 1% to 100% by volume at a pressure of 0.2~0.5 MPa and a gas hourly space velocity of hydrogen diluted with nitrogen of 2400 hour$^{-1}$. The catalyst was pre-reduced by raising the temperature of the system from room temperature to 290°±5° C. at an average speed of less than 10° C. per hour, for 10 hours.

The reaction of a solution of maleic anhydride and n-butanol at a molar ratio of anhydride to alcohol of 1:2.5 was carried out at a vaporization temperature of 170°±5° C. under the following conditions: 0.5 MPa, the temperature at the outlet of the reactor of 270°±5° C., the liquid hourly space velocity of feedstock anhydride of 0.1 hour$^{-1}$ and the molar ratio of hydrogen to anhydride of 250:1. A sample was taken from the reactor when the reaction was carried out for 1500 hours, and the sample was analyzed with the results listed below: the conversion of maleic anhydride was 98 mol %; the selectivity to product γ-butyrolactone was 85 mol %; the selectivity to by-product tetrahydrofuran was about 8 mol %, and the rest of the by-products were chiefly butyl butyrate.

EXAMPLE 3

The catalyst particles of example 2, which was pulverized to 10~18 mesh, were used.

The catalyst was pre-reduced at the same packing amount and in the same pre-reduction method as those described in example 1. The feed composition and the size of the reactor during the reaction was the same as those in example 1, except that the vaporization of the feed was carried out in a counter-current vaporizer independent of the reactor at a vaporization temperature of 200° C. The reaction conditions were as follows: 0.8 MPa, 255°±3° C., the liquid hourly space velocity of the feedstock anhydride of 0.15 hour$^{-1}$ and the molar ratio of hydrogen to anhydride of 250:1. The reaction products were analyzed with the results listed below: the conversion of maleic anhydride was 99 mol %; the selectivity to product γ-butyrolactone was 90 mol %; the selectivity to by-product tetrahydrofuran was about 7 mol %, and the rest of the by-products were chiefly 1,4-butanediol.

EXAMPLE 4

The catalyst, its packing amount and its pre-reduction method, the reaction equipment and the feed composition used in this example were similar to those described in example 3. The vaporization temperature was 200° C. The reaction was carried out under the following conditions: 1.0 MPa, 265°±3° C., the liquid hourly space velocity of the feedstock anhydride of 0.24 hour$^{-1}$ and the molar ratio of hydrogen to anhydride of 250:1. The reaction products were analyzed with the results listed below: the conversion of maleic anhydride was 98 mol %; the selectivity to product γ-butyrolactone was 85 mol %; the selectivity to by-product tetrahydrofuran was about 10 mol %, and the rest of the by-products were chiefly 1,4-butanediol.

EXAMPLE 5

It is proved in this example that the catalyst which is compatible with the process of the present invention possesses good regeneration property.

The catalyst used in the experiment was the catalyst of example 1 which had been deactivated. The reactor of example 1 was packed with the said catalyst, and the temperature of the reactor was reduced to room temperature. The catalyst was activated by gradually raising the temperature of the reactor to 295°±5° C. at a pressure of 0.8 MPa and at a gas hourly space velocity of air of 2400 hour$^{-1}$ for regeneration, during which the average velocity of temperature increment was 5° C. per hour in a temperature range between 150° and 200° C., and was 10° C. per hour above 200° C., then the catalyst was continuously activated by gradually substituting air with pure oxygen for 14 hours, and the total activation-regeneration time was about 54 hours. The regenerated catalyst was pre-reduced in the process described in example 1, then the reaction was carried out. The reaction results of the fresh catalyst, the deactivated catalyst prior to regeneration and the regenerated catalyst after regeneration at a pressure of 0.8 MPa, at a molar ratio of hydrogen to anhydride of 250:1 and at a liquid hourly space velocity of feedstock anhydride of 0.1 hour$^{-1}$ were listed in Table 1.

TABLE 1

|  | Reaction Conversion | | Selectivity (mol %) | | | |
| --- | --- | --- | --- | --- | --- | --- |
|  | Temperature (°C.) | (mol %) | γ-Butyro-lactone | Tetrohydro-furan | 1,4-Butane-diol | n-butanol |
| Fresh catalyst | 265 | 98 | 92 | 6 | 2 | — |
| Deactivated catalyst | 280 | 97 | 89 | 4 | 2 | 5 |
| Regenerated catalyst | 268 | 98 | 90 | 3 | 2 | 5 |

We claim:

1. A process for vapor phase hydrogenation of maleic anhydride and/or succinic anhydride to γ-butyrolactone, comprising contacting an alcoholic solution of the feedstock anhydride with reduced Cu-Zn-Cr-Zr catalyst under the conditions of vapor phase hydrogenation.

2. A process according to claim 1, characterized in that said alcoholic solution of the feedstock anhydride is the solution of the feedstock anhydride and saturated $C_1$–$C_4$ monohydric alcohol at a molar ratio of 1:1~4.

3. A process according to claim 1, characterized in that the hydrogenation is carried out under the conditions of the molar ratio of hydrogen to anhydride of 50–300, the temperature range between 200° and 300° C., the pressure range between 0.1 and 2.0 MPa, and the liquid hourly space velocity of the feedstock anhydride of 0.04~0.30 hour$^{-1}$.

4. A process according to claim 1, characterized in that the catalyst has the following oxide formula: $Cu_aZnCr_bZr_cO_x$, wherein a, b and c represent the atom number of Cu, Cr and Zr respectively, a=0.1~10, b=c=0.1~5, and x is the number of oxygen atoms necessary to satisfy the valency requirements of the other metal elements.

5. A process according to claim 1, characterized in that the reduction of catalyst is carried out in hydrogen or inert gas diluted hydrogen at the temperature range between 150° and 300° C. and the pressure range between 0.1 and 2.0 MPa for 5–40 hours.

6. A process according to claim 1, characterized in that the process is carried out in a fixed bed reactor, which can be either a single reactor or a reactor group consisting of two cascade reactors.

7. A process according to claim 6, characterized in that, in the case of the cascade reactors, the feed hourly space velocity in the first reactor is at least twice as much as that in the second reactor.

8. A process according to claim 1, further comprising that, after the reaction, the effluent is separated by condensation and rectification to obtain the target product γ-butyrolactone and a small amount of by-products, and that the excess alcohol and hydrogen are recovered for use in circulation.

9. A process for vapor phase hydrogenation of maleic anhydride and/or succinic anhydride to γ-butyrolactone, comprising vaporizing a solution of the feedstock anhydride and a saturated $C_1$–$C_4$ monohydric alcohol at a molar ratio of 1:1~4, then contacting under hydrogenation conditions with a reduced catalyst having the following oxide formula prior to reduction: $Cu_aZnCr_bZr_cO_x$, wherein a, b and c represent the atom number of Cu, Cr and Zr respectively, a=0.1~10, b=c=0.1~5, and x is the number of oxygen atoms necessary to satisfy the valency requirements of the other metal elements.

10. A process according to claim 9, characterized in that the hydrogenation is carried out under the conditions of the molar ratio of hydrogen to anhydride of 50–300, the temperature range between 200° and 300° C., the pressure range between 0.1 and 2.0 MPa, and the liquid hourly space velocity of the feedstock anhydride of 0.04~0.30 hour$^{-1}$.

11. A process according to claim 9, characterized in that the reduction of the catalyst is carried out in hydrogen or inert gas diluted hydrogen at the temperature range between 150° and 300° C. and the pressure range between 0.1 and 2.0 MPa for 5~40 hours.

12. A process according to claim 9, characterized in that the process is carried out in a fixed bed reactor, which can be either a single reactor or a reactor group consisting of two cascade reactors.

13. A process according to claim 12, characterized in that, in the case of the cascade reactors, the feed hourly space velocity in the first reactor is at least twice as much as that in the second reactor.

14. A process according to claim 9, further comprising that, after the reaction, the effluent is separated by condensation and rectification to obtain the target product γ-butyrolactone and a small amount of by-products, and the excess alcohol and hydrogen is recovered for use in circulation.

* * * * *